United States Patent [19]

Copelan

[11] Patent Number: 5,039,616
[45] Date of Patent: Aug. 13, 1991

[54] METHOD FOR PREVENTION OF SPECIMEN TAMPERING IN SUBSTANCE ABUSE TESTING AND TEST AREA RELATING THERETO

[76] Inventor: Herbert W. Copelan, 8706 Via Reale, Boca Raton, Fla. 33496

[21] Appl. No.: 401,107

[22] Filed: Aug. 31, 1989

[51] Int. Cl.$^5$ .................... G01N 33/94; G01N 37/00
[52] U.S. Cl. ........................................ 436/56; 4/661;
52/33; 52/34; 128/749; 128/34; 358/108;
422/61; 436/174; 436/180; 436/901
[58] Field of Search ................ 436/56, 901, 174, 180;
422/100, 61, 102; 358/108, 109; 52/6, 33, 34;
4/661; 128/749, 760, 771; 424/9

[56] References Cited

U.S. PATENT DOCUMENTS 4,223,004 9/1980 Hsia et al. .............................. 436/56
4,769,215 9/1988 Ehrenkranz ..................... 422/102 X Primary Examiner—Robert J. Hill, Jr.
Attorney, Agent, or Firm—Dann, Dorfman, Herrell and Skillman

[57] ABSTRACT

This invention provides a method and a test area to prevent tampering in the collection of specimens for substance abuse testing from a subject utilizing a specimen collection container. More particularly, the present invention prevents the substitution of the subject by another person and prevents the subject from introducing a previously obtained and concealed false specimen while minimizing intrusion on the subject's privacy.

39 Claims, 2 Drawing Sheets

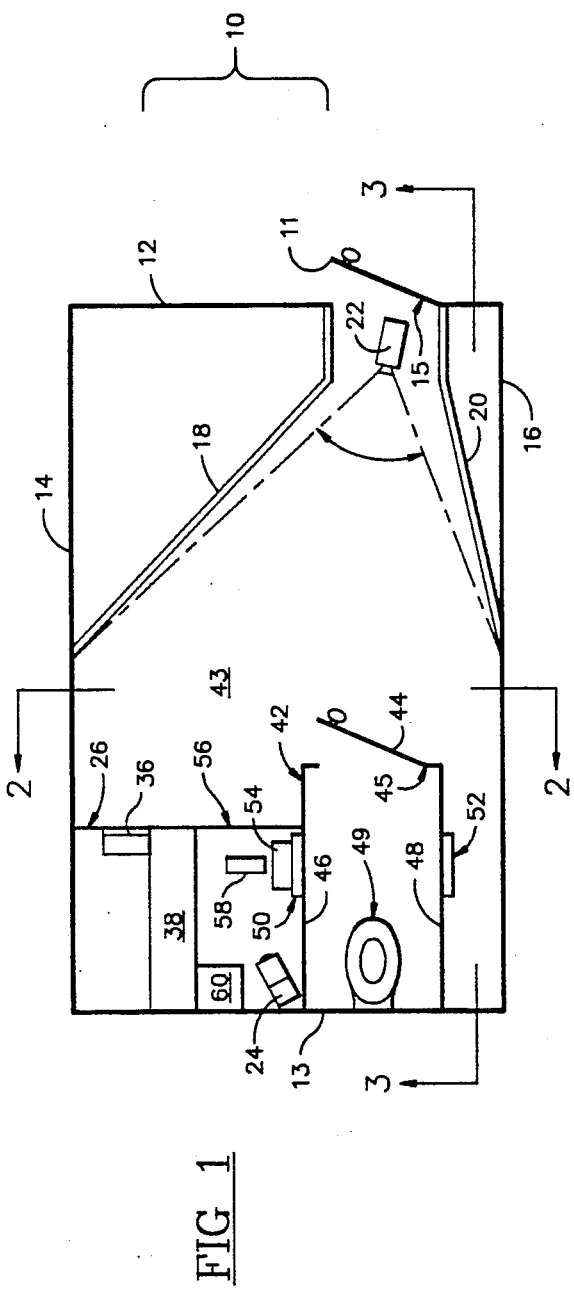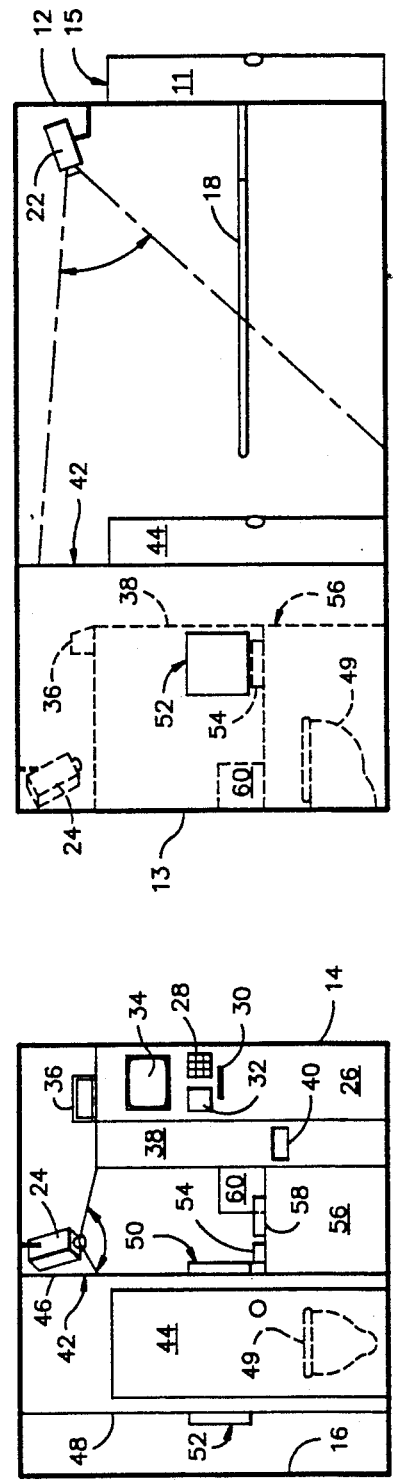

METHOD FOR PREVENTION OF SPECIMEN TAMPERING IN SUBSTANCE ABUSE TESTING AND TEST AREA RELATING THERETO

BACKGROUND OF THE INVENTION

This invention relates to a method and a test area to prevent tampering in the collection of specimens for substance abuse testing and, more particularly, to prevent tampering in the collection of specimens for substance abuse testing from a subject utilizing a specimen collection container.

In recent years, a considerable amount of attention has been focused on the social and economic, as well as other, consequences of substance abuse, that is, the use of illegal drugs, the illegal or deleterious use of legally controlled drugs, or the deleterious use of freely available drugs including alcohol. The efforts to control and eradicate substance abuse and the consequences thereof encompass many diverse strategies, however, a feature common to many of these approaches places a strong emphasis on the testing of specimens from human subjects to determine whether substance abuse has occurred. Not only is such testing conducted as part of many programs concerned with matters in the nature of drug/alcohol rehabilitation and probation and parole of criminal offenders (e.g., no substance abuse as a condition of parole; drunk driving) but it is also increasingly required as a condition of gaining or retaining employment, particularly where safety or integrity is important (e.g., airline pilots, railroad engineers, truck drivers, and public officials). In each case, the subject who abuses such substances has a considerable social and financial incentive to tamper with specimens which would indicate substance abuse upon testing, that is test positive. For instance, depending on the subject's circumstances, a positive test could mean denial or loss of employment and therefore income, dismissal from military service, change in parole or probation status, criminal prosecution, designation as a chronic abuser, and/or designation as a security risk.

In order to foil detection a subject may tamper with a substance abuse test in at least two ways. One way is to substitute another person, one who is not a substance abuser, for the actual subject. Another way is for the subject to introduce a false specimen instead of his own during the specimen collection process. A false specimen is defined as: a specimen given by the subject at a prior time when drug-free; a specimen obtained by the subject from another person; or a substance with properties similar to that of a specimen; which is free of detectable amounts of the substance that is to be tested for, and which is concealed beforehand and introduced by the subject instead of a valid specimen.

Concerns for protecting the fundamental privacy and dignity of subjects dictate against direct observation of the subject during specimen collection as a means of preventing introduction of a false specimen. While protecting the important privacy interests of subjects, presently known methods overly rely on the individual honesty of subjects and attendant personnel thus presenting a variety of opportunities for tampering. Identification procedures are not always rigorous and a substitute may appear instead of the true subject. If the identification procedure is adequate, a dishonest or lax attendant may not adhere to it. If the subject is properly identified, subsequent inadequate or dishonest supervision of the testing area may allow someone else to substitute for the subject. Finally, as mentioned hereinabove, a properly identified subject, particularly in the privacy of a toilet, may introduce a false specimen obtained and concealed beforehand. Thus, recent studies show that up to 40 percent of urine specimens given in employee substance abuse testing programs are false. Presently known methods of specimen collection rely on measuring specimen temperature and comparing it to normal body temperature to determine whether or not a specimen is false. These methods, however, permit subjects to successfully introduce false specimens with ease. For instance, old, drug-free samples of the subject's urine or substances having properties (e.g., pH, color, density) similar to urine are held under the armpit by the subject in order to raise the false specimen's temperature to approximately body temperature, thus foiling detection.

SUMMARY OF THE INVENTION

It is therefore a principal object of the present invention to provide a method which prevents the substitution of the subject by another person and prevent the subject from introducing a previously obtained and concealed false specimen, and to accomplish this while minimizing intrusion on the subject's privacy.

It is a further object of the present invention to provide a test area which enables the method of this invention to be used.

The test area of the present invention comprises a registry, which is preferably computerized; a toilet compartment having a closable entrance and at least one toilet compartment sidewall, said sidewall having at least one aperture assembly containing an aperture, said toilet compartment preferably having a first toilet compartment sidewall and a second toilet compartment sidewall, preferably the first sidewall having a first aperture assembly containing a first aperture and the second sidewall having a second aperture assembly containing a second aperture; a connecting area between said registry area and said toilet compartment; a specimen collection container dispenser; a specimen collection container deposit area; and preferably at least one monitoring camera so positioned in said test area such that the monitoring camera views substantially all of the registry, the closable entrance of the toilet compartment, the connecting area therebetween, the interior of the toilet compartment when the entrance is open, the aperture assembly, and the specimen collection container deposit area to enable essentially continuous monitoring of the subject from the start of subject identification until the subject discharges a specimen into the specimen collection container and deposits, in accordance with a prescribed deposit procedure, the filled specimen collection container in the deposit area. Monitoring by attendant personnel in lieu of, or in addition to, the monitoring camera is also contemplated.

The method of the present invention, for preventing tampering in the collection of a specimen from a subject utilizing a container for use by the subject to either receive the specimen or to dispense a tagging substance for ingestion by the subject, comprises the steps of (a) identifying a subject using an individual-specific subject identification; (b) delivering said container to said subject and preventing substitution of the container or the identified subject by essentially continuously monitoring the identified subject and the container until the identified subject effects proper use of the container and relinquishes the container; and (c) preventing introduction of a false specimen. According to the present invention, introduction of a false specimen is prevented by measuring predetermined physicochemical characteristics of the specimen collected from the subject, that is, by measurement of specimen temperature, and/or by administration of a tagging substance to the subject, followed by measurement of the collected specimen for the presence or amount thereof. Also according to the present invention, introduction of a false specimen is prevented by restricting the actions of the identified subject while the subject is within the closed toilet compartment, or by any combination of the foregoing methods.

BRIEF DESCRIPTION OF THE DRAWINGS

The foregoing summary and the following detailed description of the invention will be better understood when read in conjunction with the accompanying drawings, in which:

FIG. 1 is a diagrammatic plan view of a test area constructed in accordance with one embodiment of the invention;

FIG. 2 is a diagrammatic sectional view along line 2—2 of FIG. 1;

FIG. 3 is a diagrammatic sectional view along line 3—3 of FIG. 1;

DETAILED DESCRIPTION OF THE INVENTION

Figure 4:
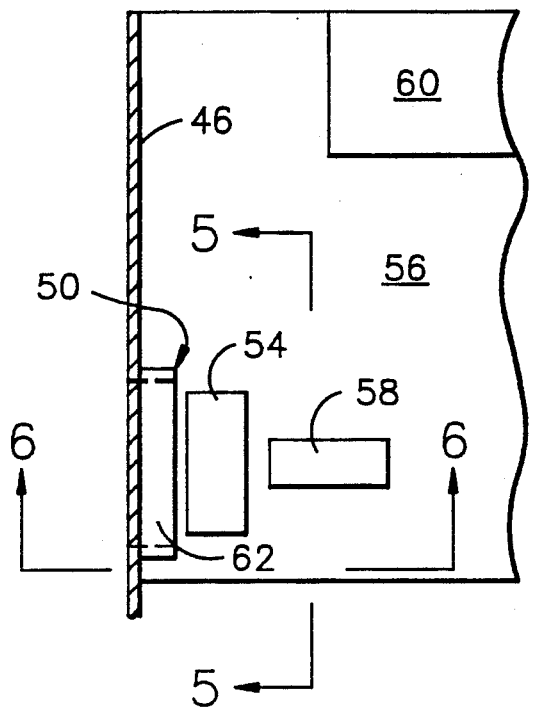
FIG. 4 is a fragmentary diagrammatic plan view illustrating the specimen collection container deposit area and the first aperture assembly.

Referring to the drawings, FIG. 1 generally illustrates one embodiment of the test area of the present invention, designated generally as 10.

The test area 10 of the preferred embodiment of the present invention includes a closable entrance 15 leading to a computerized registry 26, a toilet compartment 42 having a toilet 49, a closable entrance 45 and a first toilet compartment sidewall 46 and a second toilet compartment sidewall 48, the first sidewall 46 containing a first aperture assembly 50, the second sidewall 48 containing a second aperture assembly 52; a connecting area 43 between the registry and the toilet compartment; a specimen collection container deposit area 56; and a first monitoring camera 22 and a second monitoring camera 24 so positioned in the test area that the cameras together substantially view the registry area 26, the closable entrance of the toilet compartment 42, the connecting area 43 therebetween, the first aperture assembly 50, the second aperture assembly 52, and the specimen collection container deposit area 56 to enable continuous monitoring of the subject from the start of subject identification until the subject voids a specimen into a specimen collection container and deposits, in accordance with a prescribed deposit procedure, the filled specimen collection container in the deposit area 56. The word "specimen" as used herein includes body fluids such as urine, blood, semen, and saliva. In the description that follows, the invention will be described with reference to collection of a urine specimen. Those skilled in the art will understand that the present invention may be readily utilized for the collection of specimens of the body fluids including saliva, semen, and blood.

More generally, the architecture of a particular test area is influenced by a number of factors including cost, importance of the testing, and the incentives for deception by the particular subject population. The technology required to construct the various embodiments of the test area is well known, readily available, and is usable with little or no modification. In the preferred embodiment, as illustrated in FIGS. 1, 2, and 3, the rectangular, enclosed test area 10 comprises a first sidewall 14 and a second sidewall 16, each connected to a rear wall 12 having a hinged first door 11 attached thereto and a front wall 13. The subject enters the test area through a first door 11 and approaches the computerized registry 26 while being kept within the view of a first monitoring camera 22 by a first barrier rail 18 and a second barrier rail 20, each rail having two ends, each rail being fixedly attached at one end to rear wall 12 and at the other end to first sidewall 14 and second sidewall 16, respectively. The registry is preferably computerized, thereby permitting automated subject identification. In the preferred embodiment illustrated in FIG. 2, registry 26, which is operable by the subject, includes a keyboard 28 and a registry card-reader 30 with which the subject may enter a previously assigned identification number on the registry computer. Instructions are transmitted automatically to the subject via message screen 34, however, such instructions, or any other necessary information, may be communicated to the subject via screen 34 or an intercom by attendant personnel. The registry preferably includes an automated scanner 32 able to scan a substantially individual-specific physical characteristic of the subject, and compare the determined characteristic with a pre-existing record of the substantially individual-specific physical characteristic for the purpose of subject identification. Preferably, this substantially individual-specific characteristic is the palm-crease pattern of the subject's hand. The palm-crease pattern is a physical characteristic that is practical for automated identification. Optical scanning of the palm pattern has already been applied to medical screening. It can be used to confirm individual identities because the variability of palm patterns allows the detection of individual differences with ample sensitivity. The scan is immediate, simple to perform, independent of an attendant, and is readily computer coded. The subject is merely required to place a hand on the scanning plate 32 for a few seconds. The scan does not require ink or stain, and does not have the unpleasant connotation of fingerprinting. The scan is coded digitally and compared automatically with the on-file pattern. A match can be used to dispense containers automatically while a mismatch may be signalled to a responsible authority.

In special situations, thumb-printing may be used as one alternative to palm-scanning. Its accuracy exceeds the requirements for testing, and it is more acceptable to many subjects than full fingerprinting. Thumb-printing can be performed by an untrained subject. A staining pad and a print blank are dispensed by the registry. The thumb is pressed on the pad and then on the blank. The print is scanned and processed in the same way as the palm-crease pattern.

Although not presently as practical as palm-scanning or thumb-printing, other individual-specific physical characteristics may possibly be used in subject identification. Such characteristics include visual patterns of the ear, iris, and entire face; dental patterns; voice profiles; and conventional fingerprints among others.

Depending on whether or not the scan and on-file physical characteristics match, the registry is equipped to perform a set of preselected actions. If there is a match, the preselected action includes assignment of an identifying indicia, such as an identification number to the specimens to be collected and causing container dispenser 38 to automatically dispense and/or label, with subject-specific information including date, time, file number, and specimen number, a specimen collection container. The preselected action may also include causing dispenser 38 to dispense a container holding a predetermined amount of an ingestible tagging substance of known composition. If there is a mismatch, the preselected action may include recordation of the mismatch in the subject's registry file. Such recordation can include notification of a responsible authority concerning the mismatch.

The test area monitoring camera can be controlled and/or viewed from a monitoring station which can be in a location remote from the test area. Such a camera may be continuously or periodically monitored by attendant personnel. The camera can also record whatever it views, thus allowing relief or total replacement of attendant personnel who view the camera image by periodic review of the recorded images at some time after the actual specimen collection occurs. The camera record includes a display, preferably continuous, of the date and time, the latter preferably to the second. Preferably, the date and time are continuously recorded by at least one monitoring camera from the date-time display 36, fixedly mounted on the registry. Monitoring by attendant personnel in lieu of, or in addition to, the monitoring camera is also contemplated.

The toilet compartment of the test area provides the subject with privacy while voiding a specimen for collection. These test specimens are usually urine specimens and preferably the design of the toilet compartment reflects this fact. To prevent the introduction of a false specimen by an identified subject, having a first hand and a second hand, in the privacy of the closed toilet compartment, means for hand monitoring may be used to restrict the subject's actions. The toilet compartment has at least one wall which contains at least one aperture assembly, viewable by the monitoring camera. The subject must insert his first hand through an aperture such that the hand is viewable by a monitoring camera. Only then may the subject insert his second hand through the same aperture or a second aperture to retrieve the empty specimen collection container dispensed from dispenser 38 and placed on a specimen collection container holder which is exterior with respect to the toilet compartment and adjacent an aperture. The specimen collection container holder can be a bottle holder, rack, small platform, or similar device.

Figure 5:
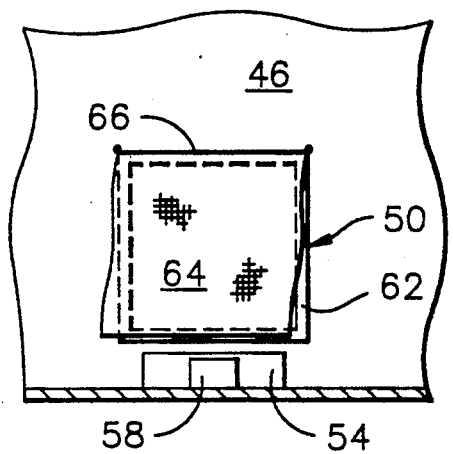
FIG. 5 is a face view along line 5—5 of FIG. 4 illustrating the first aperture assembly.
Figure 6:
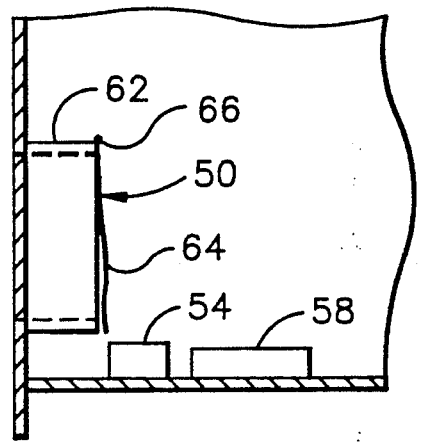
FIG. 6 is a fragmentary sectional view along line 6—6 of FIG. 4 illustrating the first aperture assembly.

In the preferred embodiment, a first toilet compartment sidewall 46 and a second toilet compartment sidewall 48 are connected at one end to front wall 13 and define at the other end a closable entrance 45 therebetween, said entrance being closable by a door 44. Sidewalls 46 and 48 contain, respectively, a first aperture assembly 50 and a second aperture assembly 52. The sidewalls 46 and 48 are approximately in line with the viewing axes of monitoring cameras 22 and 24. The plane of the aperture of each aperture assembly being approximately parallel to the viewing axes of cameras 22 and 24, the apertures themselves are not directly visible by either camera. In the preferred embodiment, illustrated diagrammatically in FIGS. 4, 5, and 6, each aperture assembly comprises a collar 62 to which is mounted a flap 64, of cloth, plastic or other suitable material, by flap hinge 66. The flap provides subjects with a greater sense of privacy. If a toilet compartment sidewall, and the aperture assembly contained therein are aligned with a monitoring camera viewing axis such that the aperture is at least partially viewable directly by a monitoring camera, the width of collar 62 may be adjusted such that any direct camera view of the aperture is obstructed by the collar.

In the preferred embodiment, the subject, upon proper identification, is dispensed a specimen collection container by container dispenser 38. The subject then places the container in specimen collection container holder 54 and only then enters the toilet compartment. Once the subject closes the door 44, the subject must insert one hand through second aperture assembly 52 such that the hand is visible to camera 22. Only then may the subject insert the other hand through the first aperture assembly 50 and retrieve the specimen collection container in view of at least one monitoring camera. Alternatively, upon closing the toilet compartment door, the subject may be permitted to insert one hand through aperture assembly 50 such that the hand is visible to camera 22 and then insert the other hand through the same aperture assembly to retrieve the specimen collection container in view of at least one monitoring camera. Introduction of a false specimen is prevented by restricting the subject's actions in that the subject is required to keep the one free hand in view of a monitoring camera at all times that the specimen collection container is inside the toilet compartment and thus not in view of a monitoring camera. Each aperture should be large enough to accommodate both of the subject's hands and the specimen collection container simultaneously so as to allow the subject to change the hand holding the container while at least one hand is continuously monitored.

Alternatively, for greater privacy, the subject can be restricted to the use of one hand for specimen collection without being required to keep the free hand in view of the monitoring camera, by use of a means for hand monitoring located within the toilet compartment. The subject may be required to keep the free hand emplaced continuously upon a full-hand contact or five-finger contact signalling device until a predetermined instance. If the subject fails to maintain contact with the signalling device for the appropriate time, the device signals a responsible authority and preferably records the event in the subject's registry record. The predetermined instance includes the point at which the subject returns the specimen collection container to the view of a monitoring camera.

The freedom of movement of the subject's hand used for specimen collection, which is not continuously monitored, may be further restricted by use of a suitably shaped and equipped specimen collection container. Two features of such a container require this hand to be completely occupied or engaged in holding the container in order for the subject to be able to void into it. First, the container is shaped such that it cannot stand unsupported and must be held upright to be filled. For example, such a container may have a bottom shape which approximates a hemisphere, parabola, cone, or elliptically truncated cylinder. Second, the container is constructed so that it must be held open to be filled. The subject, therefore, cannot use the unmonitored hand to introduce a false specimen into the specimen collection container while in the privacy of the toilet compartment.

The filled specimen collection container is deposited by the subject in the specimen collection container deposit area 56. Preferably, the deposit area 56 is equipped with a deposit receptacle 58 from which filled containers are not retrievable by the subject. The deposit area is preferably equipped to measure and record the temperature of the specimen upon deposit. The temperature of freshly voided urine specimens is limited to the narrow range of the body's core temperature, which is usually above ambient temperature. If the specimen is significantly outside such predetermined temperature range, it is not fresh and cannot be a true specimen for the test. To duplicate body temperature in a substituted specimen, the subject would need to perform several actions. The subject would need to adjust the false specimen rather precisely to body temperature, store and keep the specimen (e.g., urine) in a concealed container while maintaining the narrow temperature range, remove and open the container of the false specimen and introduce the false specimen into the specimen collection container.

Specimen temperature measurement using readily available technology permits interdiction of such false specimens. In one embodiment, the specimen temperature is measured by internal means for temperature measurement inaccessible to the subject. The term "internal" comprehends means which are specific to a particular specimen collection container. Such means include a clinical-type thermometer which is automatically dispensed to the subject in the deposit area and inserted by him into the container under surveillance by the monitoring camera. A clinical-type thermometer, which records within its range only the maximum temperature to which it is exposed, is preferred because urine temperature decreases rapidly after voiding, and the object is to insure that the specimen is freshly voided. This type of thermometer requires that the container be stored where the ambient temperature is below the temperature range of the human body. In another embodiment, the clinical-type thermometer is fixedly attached to the closure or top of the specimen collection container. In either case, the temperature measuring device is not dispensed, available or used until the specimen is brought into view of the monitoring camera.

In another embodiment, specimen temperature is measured by an external means for temperature measurement. The term "external" refers to temperature measurement devices which are not specific for each individual specimen collection container but rather to devices 60 installed in the deposit area which measure specimen temperature when applied to the specimen collection container or the contents thereof under surveillance by the monitoring camera. Such means include thermocouples and similar devices.

If visual monitoring is not used the temperature should not be measured and recorded until the filled container is closed and cannot be reopened by the subject. A thermocouple or other temperature-measuring device can then record the temperature of each specimen at the time it is deposited. Alternatively, an individual clinical-type thermometer in the top or body of the container may be used. Such thermometer must not be accessible to the subject or exposed to the specimen until closure by a seal or catch that reveals any subsequent reopening. Devices that accomplish this include a thermometer with a connection completed by closing the container or one with a shield that is stripped by the action of closure.

The method of the present invention, for preventing tampering in the collection of a specimen from a subject utilizing a container for use by said subject to either receive the specimen or to dispense a tagging substance for ingestion by said subject, comprises the steps of:

(a) identifying a subject using an individual-specific subject identification;

(b) delivering said container to said subject and preventing substitution of the container or said identified subject by essentially continuously monitoring said identified subject and the container until said identified subject effects proper use of the container and relinquishes said container; and (c) preventing introduction of a false specimen. According to the present invention, introduction of a false specimen is prevented by measuring predetermined physicochemical characteristics of the specimen collected from the subject, that is, by measurement of specimen temperature, and/or by administration of a tagging substance to the subject followed by measurement of the collected specimen for the presence or amount thereof. Also according to the present invention, introduction of a false specimen is prevented by restricting the actions of the identified subject while the subject is within the closed toilet compartment, or by any combination of the foregoing methods.

Verification of the subject's identity is essential to prevent specimen tampering in a substance abuse testing program. Preferably, the method of the present invention correctly identifies the subject automatically by use of a computerized registry, hereinbefore described. Advantageously, the present method does not depend on the honesty of the subject or attendant personnel. In the preferred embodiment, the subject uses a registry keyboard or a card-pass and registry card-reader to enter a previously issued subject-specific file number. In practice, the card can include a digitalized description of the subject's identifying substantially individual-specific physical characteristic to reduce registry file space requirements and file costs, as well as to reduce error and to speed identification. The registry determines a substantially individual-specific physical characteristic of the subject, compares the determined characteristic with a pre-existing record of that physical characteristic, and then performs a preselected action involved in initiating the specimen collection procedure. Preferably, the substantially individual-specific physical characteristic utilized for identification purposes is the subject's palm-crease pattern, detected by an optical scanner as hereinbefore described. The registry preferably records a variety of data including date and time of the subject's appearance, the subject's file number, the digital description of the subject's substantially individual-specific physical characteristic, the results of the comparison between the determined physical characteristic and the pre-existing record of that physical characteristic, and the time and container identification number, if any, whenever any container is dispensed or deposited. The preselected action includes dispensing of a specimen collection container only when said determined substantially individual-specific physical characteristic matches the pre-existing record of that physical characteristic. Also, the preselected action can include labelling the specimen collection container with indicia when the determined physical characteristic matches the pre-existing record of the physical characteristic. The container label preferably includes the subject file number as well as an individual container identification number. Additionally, the pre-selected action can include notification of a responsible authority when the determined physical characteristic does not match the pre-existing record of the physical characteristic. Preferably, the occurrence of such a mismatch is recorded in the subject's registry file.

To prevent another person from substituting for the identified subject, preferably a monitoring camera, hereinbefore discussed, monitors the subject continuously while the subject is in the test area from the time the identification procedure starts until the filled specimen collection container is deposited properly, or a tagging substance is ingested by the subject thereby eliminating the need for further subject observation in the test area. Once the identified subject has ingested a tagging substance, the subject need no longer be monitored. Analysis of the subject's specimen for the tagging substance will reveal whether substitution of the specimen, the specimen collection container or of the identified subject has occurred.

The method of the present invention contemplates preventing introduction of a false specimen, hereinbefore defined, by the subject while in the privacy of the toilet compartment, by use of any combination of the following means. According to the present invention, introduction of a false specimen is prevented by restricting the actions of the identified subject while the subject is within the closed toilet compartment, by measurement of specimen temperature, and/or by administration of a tagging substance to the subject. Advantageously, the present method prevents false specimen introduction while protecting the subject's privacy interest and dignity during specimen collection.

In the ingested-tagging substance embodiment, a tagging substance, ingested by the subject during a predetermined period before voiding the specimen, identifies the specimen as that of the actual subject, voided during the test period. The present method, utilizing this procedure, comprises the steps of:

(a) assigning a predetermined amount of said ingestible tagging substance of known composition to said subject for said specimen to be collected;

(b) recording said assignment in a registry file also containing identifying information on said subject;

(c) administering said tagging substance to said subject upon subject identification, whereby said tagging substance becomes present in a body fluid from which said specimen is collected;

(d) collecting said specimen from said subject;

(e) determining the presence or amount of said tagging substance in said specimen;

(f) comparing the results of said tagging substance determination with said recorded assignment and identifying information.

Preferably, three containers are dispensed to the subject under camera surveillance either sequentially, or together if identifiably different to the monitoring camera, to insure use in the correct order. The first container is preferably sealed and contains the tagging substance, preferably in liquid form. The subject ingests the tagging substance in view of the monitoring camera, inverts the empty container for the camera to view and deposits the container in a receptacle that prevents unauthorized retrieval. The second container, preferably sealed, is filled with water and is similarly ingested, inverted and deposited in view of the camera. These steps insure that only the subject has access to the tagging substance assigned to him and that he ingests it. Finally, the specimen collection container is dispensed and monitoring of the subject can be terminated. This method advantageously does not require monitoring once the tagging substance is ingested, allowing the subject a period of freedom in which to void the specimen.

Tagging substances may include a broad variety of food dyes, commercial flavors, vitamins, trace elements and other harmless substances or their isomers. Tagging substances may be identified by known techniques such as mass spectrometry at the time the specimen is tested for abused substances. Even if a subject could discover the identities of all the tagging substances used in a testing program, the chance of matching a specific subject's tagging group would be prohibitively small. The probability for such a match is limited by the number of different tagging substances, and the number of combinations thereof, used for the entire subject population and the number of tagging substances administered to each subject. A specimen may be collected immediately before the tagging substance is dispensed; comparing this specimen with the one collected after the tagging substance is ingested eliminates the possibility of confusion or deception if a substance similar to the tagging substance is ingested before the test.

Introduction of a false specimen while in the privacy of a toilet compartment can be made difficult by restricting one hand of a subject having a first hand and a second hand, thereby limiting him to the use of one hand only when filling the specimen collection container. The present method, utilizing this hand-restriction procedure, comprises the following steps:

(a) providing a toilet compartment having a first toilet compartment sidewall, the sidewall having at least one aperture assembly containing an aperture, which assembly is visible to a monitoring camera;

(b) causing the subject to place an empty specimen collection container adjacent to the aperture such that the container is visible to the monitoring camera;

(c) causing the subject to enter the toilet compartment;

(d) causing the subject to expose the first hand to means for hand monitoring until the subject completes steps (e)-(g);

(e) causing the subject to bring the specimen collection container inside the toilet compartment through the aperture by use of the second hand;

(f) causing the subject to discharge the specimen into the specimen collection container;

(g) causing the subject to place the filled specimen collection container outside of the toilet compartment through an aperture such that the container is visible to the monitoring camera;

(h) causing the subject to remove the first hand from exposure to the means for hand monitoring and to exit the toilet compartment.

In one embodiment wherein said toilet compartment is provided with only the first aperture assembly defining a first aperture, the means for hand monitoring include causing the subject to pass the first hand through the aperture such that the hand is viewable by a monitoring camera. In the preferred embodiment, the means for hand monitoring include a second aperture assembly defining a second aperture in the toilet compartment wall, or preferably in the second toilet compartment wall, through which the first hand is passed such that it is viewable by the monitoring camera as hereinbefore described.

Alternatively, for greater privacy, the subject can be restricted to the use of one hand without being required to keep one hand in view of the monitoring camera by use of a means for hand monitoring located within the toilet compartment. The subject is required to keep his first hand emplaced upon a full-hand contact or five-finger contact signalling device until a predetermined instance. If the subject fails to do so, the device signals a responsible authority and preferably records the event in the subject's registry record. The predetermined instance includes the point at which the subject returns the specimen collection container to the view of the monitoring camera.

The subject's second hand, which is not continuously monitored, may be further restricted by use of a suitably shaped and equipped specimen collection container. Two features of such a container require this hand to be completely engaged in holding the container while the subject voids into it. First, the container is shaped such that it cannot stand unsupported and must be held upright to be filled. For example, such a container may have a bottom shape which approximates a hemisphere, parabola, cone, or elliptically truncated cylinder. Second, the container is constructed so that it must be held open to be filled. The subject, therefore, cannot use the unmonitored hand to introduce a false specimen into the specimen collection container and thus does not have either hand free while filling the container within the privacy of the toilet compartment.

The terms and expressions which have been employed are used as terms of description and not of limitation, and there is no intention in the use of such terms and expressions of excluding any equivalents of the features shown and described, or portions thereof, but it is recognized that various modifications are possible within the scope of the invention claimed.

What is claimed is:

1. A method for preventing tampering in the collection of a specimen from a subject utilizing a container for use by said subject to either receive said specimen or to dispense a tagging substance for ingestion by said subject, said method comprising the steps of:
   (a) identifying a subject using an individual-specific subject identification;
   (b) delivering said container to said subject for administration of an ingestible tagging substance to said subject and preventing substitution of said container or said identified subject by essentially continuously monitoring said identified subject and said container until said identified subject effects proper use of said container and relinquishes said container and thereafter collecting and analyzing said specimen, to determine the presence of said tagging substance therein; and
   (c) preventing introduction of a false specimen by measuring predetermined physicochemical characteristics of said specimen collected from said subject.

2. A method as recited in claim 1, said identifying step includes:
   (i) determining a substantially individual-specific physical characteristic of said subject;
   (ii) comparing said determined substantially individual-specific physical characteristic with a pre-existing record of said substantially individual-specific physical characteristic; and
   (iii) performing a preselected action involved in initiating the specimen collection procedure.

3. A method as recited in claim 2 wherein said step of determining a substantially individual-specific physical characteristic comprises scanning a palm-crease pattern of said subject.

4. A method as recited in claim 2 wherein said preselected action includes dispensing of a specimen collection container only when said determined substantially individual-specific physical characteristic matches said pre-existing record of said substantially individual-specific physical characteristic.

5. A method as recited in claim 4 wherein said preselected action includes labeling said specimen collection container with identifying indicia only when said determined substantially individual-specific physical characteristic matches said pre-existing record of said substantially individual-specific physical characteristic.

6. A method as recited in claim 2 wherein said preselected action includes notification of a responsible authority when said determined substantially individual-specific physical characteristic does not match said pre-existing record of said substantially individual-specific physical characteristic.

7. A method as recited in claim 1, wherein said introduction prevention step comprises measuring the temperature of said specimen.

8. A method as recited in claim 7 wherein said specimen temperature is measured by temperature measurement means external to said specimen collection container.

9. A method as recited in claim 8 wherein said external means for temperature measurement includes a thermocouple device.

10. A method as recited in claim 7 wherein said specimen temperature is measured by temperature measurement means internal to said specimen collection container and inaccessible to said subject at the time specimen temperature is measured.

11. A method as recited in claim 10 wherein said specimen temperature of each said specimen collection container is individually measured by a clinical-type thermometer.

12. A method as recited in claim 10 wherein said specimen temperature is measured by a clinical-type thermometer fixedly attached to said specimen collection container.

13. A method as recited in claim 7, further comprising the steps of:
   (a) measuring specimen temperature after said subject no longer has access thereto; and
   (b) comparing said specimen temperature to normal core temperature.

14. A method for preventing tampering in the collection of a specimen from a subject utilizing a container for use by said subject to either receive said specimen or to dispense a tagging substance for ingestion by said subject, said method comprising the steps of:
   (a) identifying a subject using an individual-specific subject identification;
   (b) delivering said container to said subject and preventing substitution of said container or said identified subject by essentially continuously monitoring said identified subject and said container until said identified subject effects proper use of said container and relinquishes said container; and
(c) preventing introduction of a false specimen by administering to said subject an ingestible tagging substance and measuring the presence or amount of said tagging substance in said specimen collected from said subject.

15. A method as recited in claim 14 wherein the introduction prevention step further comprises the steps of:
(a) assigning a predetermined amount of said ingestible tagging substance of known composition to said subject for said specimen to be collected;
(b) recording said assignment in a registry file also containing identifying information on said subject;
(c) administering said tagging substance to said subject upon subject identification, whereby said tagging substance becomes present in a body fluid from which said specimen is collected;
(d) collecting said specimen from said subject;
(e) determining the presence or amount of said tagging substance in said specimen;
(f) comparing results of said tagging substance determination with said recorded assignment and identifying information.

16. A method as recited in claim 14, wherein said introduction prevention step further comprises restricting actions of said subject.

17. A method as recited in claim 14, wherein the introduction prevention step further comprises the steps of:
(i) measuring specimen temperature after said subject no longer has access thereto; and
(ii) comparing said specimen temperature to normal body core temperature.

18. A method as claimed in claim 17, wherein said introduction prevention step further comprises restricting actions of said subject.

19. A method as recited in claim 14, said identifying step comprising:
(i) determining a substantially individual-specific physical characteristic of said subject;
(ii) comparing said determined substantially individual-specific physical characteristic with a pre-existing record of said substantially individual-specific physical characteristic; and
(iii) performing a preselected action involved in initiating the specimen collection procedure.

20. A method as recited in claim 19, wherein said step of determining a substantially individual-specific physical characteristic comprises scanning a palm-crease pattern of said subject.

21. A method as recited in claim 19, wherein said preselected action includes dispensing of a specimen collection container only when said determined substantially individual-specific physical characteristic matches said pre-existing record of said substantially individual-specific physical characteristic.

22. A method as recited in claim 21, wherein said preselected action includes labeling said specimen collection container with identifying indicia only when said determined substantially individual-specific physical characteristic matches said pre-existing record of said substantially individual-specific physical characteristic.

23. A method as recited in claim 19, wherein said preselected action includes notification of a responsible authority when said determined substantially individual-specific physical characteristic does not match said pre-existing record of said substantially individual-specific physical characteristic.

24. A test area comprising a registry for subject identification, a container dispenser, said container dispenser dispensing a tagging substance container, said tagging substance container containing an ingestible tagging substance, a toilet compartment having a closable entrance and at least one toilet compartment sidewall, said sidewall having at least one aperture assembly containing an aperture, a connecting area between said registry and said toilet compartment, a specimen collection container deposit area, and at least one monitoring camera so positioned in said test area that said camera views substantially all of said registry, said container dispenser, said closable entrance of said toilet compartment, said connecting area therebetween, said at least one aperture assembly and said specimen collection container deposit area to enable continuous monitoring of said subject from the start of said subject identification during administration of said tagging substance to said subject in accordance with a prescribed administration procedure, until said subject voids a specimen into a specimen collection container and deposits, in accordance with a prescribed deposit procedure, said collection container containing said specimen in said deposit area.

25. A test area as recited in claim 24 said toilet compartment having a first toilet compartment sidewall, having a first aperture assembly containing a first aperture, and a second toilet compartment sidewall, having a second aperture assembly containing a second aperture, said first and second aperture assemblies being viewable by said monitoring camera.

26. A test area comprising a registry for subject identification, a toilet compartment having a closable entrance and at least one toilet compartment sidewall, said sidewall having at least one aperture assembly containing an aperture, a connecting area between said registry and said toilet compartment, a specimen collection container deposit area, and at least one monitoring camera so positioned in said test area that said camera views substantially all of said registry, said closable entrance of said toilet compartment, said connecting area therebetween, said at least one aperture assembly and said specimen collection container deposit area to enable continuous monitoring of said subject from the start of said subject identification until said subject voids a specimen into a specimen collection container and deposits, in accordance with a prescribed deposit procedure, said collection container containing said specimen in said deposit area and a remote monitoring station, wherein said monitoring camera is controllable and/or viewable from said remote monitoring station.

27. A test area as recited in claim 26 said toilet compartment having a first toilet compartment sidewall, having a first aperture assembly containing a first aperture, and a second toilet compartment sidewall, having a second aperture assembly containing a second aperture, said first and second aperture assemblies being viewable by said monitoring camera.

28. A method for preventing tampering in the collection of a specimen from a subject utilizing a container for use by said subject to either receive said specimen or to dispense a tagging substance for ingestion by said subject, said method comprising the steps of:
(a) identifying a subject using an individual-specific subject identification;

(b) delivering said container to said subject for administration of an ingestible tagging substance to said subject and preventing substitution of said container or said identified subject by essentially continuously monitoring said identified subject and said container until said identified subject effects proper use of said container and relinquishes said container, and thereafter collecting and analyzing said specimen, to determine the presence of said tagging substance therein; and (c) preventing introduction of a false specimen by restricting actions of said subject.

29. A method as recited in claim 28 wherein said identifying step includes:

(a) determining a substantially individual-specific physical characteristic of said subject;

(b) comparing said determined substantially individual-specific physical characteristic with a pre-existing record of said substantially individual-specific physical characteristic; and (c) performing a preselected action involved in initiating the specimen collection procedure.

30. A method as recited in claim 29 wherein said step of determining a substantially individual-specific physical characteristic comprises scanning a palm-crease pattern of said subject.

31. A method as recited in claim 29 wherein said preselected action includes dispensing of a specimen collection container only when said determined substantially individual-specific physical characteristic matches said pre-existing record of said substantially individual-specific physical characteristic.

32. A method as recited in claim 31 wherein said preselected action includes labeling said specimen collection container with identifying indicia only when said determined substantially individual-specific physical characteristic matches said pre-existing record of said substantially individual-specific physical characteristic.

33. A method as recited in claim 29 wherein said preselected action includes notification of a responsible authority when said determined substantially individual-specific physical characteristic does not match said pre-existing record of said substantially individual-specific physical characteristic.

34. A method as recited in claim 28, for use with a subject having a first hand and a second hand, wherein said introduction prevention step further comprises the steps of:

(a) providing a toilet compartment having a first toilet compartment sidewall, said sidewall having an aperture assembly containing an aperture, which assembly is visible to a monitoring camera;

(b) causing the subject to place an empty specimen collection container adjacent to said aperture such that said container is visible to said monitoring camera;

(c) causing the subject to enter said toilet compartment;

(d) causing the subject to expose said first hand to means for hand monitoring until said subject completes steps (e)-(g);

(e) causing the subject to bring said specimen collection container inside said toilet compartment through said aperture by use of said second hand;

(f) causing the subject to discharge said specimen into said specimen collection container;

(g) causing the subject to place said filled specimen collection container outside of said toilet compartment through an aperture such that said container is visible to said monitoring camera; and (h) causing the subject to remove said first hand from exposure to said means for hand monitoring and to exit said toilet compartment.

35. A method as recited in claim 34 wherein said means for hand monitoring comprises a second aperture assembly containing a second aperture in said toilet compartment wall through which said first hand is passed, such that said first hand is continuously viewable by said monitoring camera.

36. A method as recited in claim 34 wherein said means for hand monitoring comprises a second aperture assembly containing a second aperture in a second toilet compartment wall, through which said first hand is passed, such that said hand is continuously viewable by said monitoring camera.

37. A method as recited in claim 34 wherein said means for hand monitoring comprises a full-hand contact signaling device within said toilet compartment upon which said first hand is emplaced, said device signalling a responsible authority if said first hand is removed from said device before a predetermined occurrence.

38. A method as recited in claim 37 wherein said means for hand monitoring comprise a five-finger contact signalling device.

39. A method as recited in claim 34 further comprising the step of restricting said second hand of said subject by causing said subject to hold open a closure of the specimen collection container, said container having a closure which must be held open by hand in order for said container to be fillable, said container having a base shaped such that said container requires support to stand upright.

* * * * *